United States Patent
Liao et al.

(10) Patent No.: US 8,912,155 B2
(45) Date of Patent: Dec. 16, 2014

(54) METHOD FOR ANALYZING SECRETOME, BIOMARKER FOR LUNG CANCER METASTASIS, AND SIRNA COMPOUND FOR INHIBITING LUNG CANCER METASTASIS

(75) Inventors: Pao-Chi Liao, Tainan (TW); Ying-Hwa Chang, Taipei (TW); Kuo-Hsun Chiu, Tainan (TW); Yu-Shun Wu, Kaohsiung (TW); Shu-Hui Lee, Huatan Township, Changhua County (TW)

(73) Assignee: National Cheng Kung University, Tainan (TW)

( * ) Notice: Subject to any disclaimer, the term of this patent is extended or adjusted under 35 U.S.C. 154(b) by 265 days.

(21) Appl. No.: 13/338,020

(22) Filed: Dec. 27, 2011

(65) Prior Publication Data
US 2012/0270254 A1 Oct. 25, 2012

(30) Foreign Application Priority Data
Apr. 22, 2011 (TW) .............................. 100114124 A

(51) Int. Cl.
*C07H 21/02* (2006.01)
*C07H 21/04* (2006.01)
*A61K 31/70* (2006.01)
*G01N 33/68* (2006.01)
*C12N 15/113* (2010.01)
*C12Q 1/68* (2006.01)
*A61K 31/7105* (2006.01)

(52) U.S. Cl.
CPC .......... *G01N 33/6842* (2013.01); *C12N 15/113* (2013.01); *A61K 31/7105* (2013.01); *C12N 2310/14* (2013.01); *G01N 2800/7028* (2013.01)
USPC ........ 514/44 A; 536/23.1; 536/24.1; 536/24.5

(58) Field of Classification Search
None
See application file for complete search history.

(56) References Cited

U.S. PATENT DOCUMENTS

| | | | |
|---|---|---|---|
| 2007/0031844 A1* | 2/2007 | Khvorova et al. | 435/6 |
| 2008/0113351 A1* | 5/2008 | Naito et al. | 435/6 |

OTHER PUBLICATIONS

Wu et al., "Comparative Analysis of Cell Secretomes Associated with Lung Cancer Metastasis," National Cheng Kung University, Intro and pp. 30-50, http://ndltd.ncl.tw/cgi-bin/gs32/gsweb.cgi/ccd=9LLX1h/record?r1=1&h1-1 (2010) with English Abstract.
Chiu et al., "Quantitative Secretome Analysis Reveals that COL6A1 is a Metastasis-Associated Protein using Stacking Gel-Aided Purification Combined with iTRAQ Labeling," Journal of Proteome Research, Dec. 28, 2010, pp. 1110-1125.

* cited by examiner

*Primary Examiner* — Sean McGarry
(74) *Attorney, Agent, or Firm* — Muncy, Geissler, Olds & Lowe, P.C.

(57) ABSTRACT

A method for analyzing secretome, a biomarker for lung cancer metastasis, and a siRNA compound for inhibiting lung cancer metastasis are disclosed. The method for analyzing secretome of the present invention comprises the following steps: (A) collecting proteome secreted from a cell; (B) providing a purification gel, wherein the purification gel comprises a low-density layer, and a high-density layer, and the low-density layer is stacked on the high-density layer; (C) adding the proteome on the low-density layer, and separating the proteome through the low-density layer and the high-density layer of the purification gel; (D) collecting the separated proteome on the interface between the low-density layer and high-density layer, and tagging the separated proteome with a reagent after digestion; and (E) analyzing the separated proteome tagged with the reagent, and comparing an analysis result with a proteomic database.

3 Claims, 2 Drawing Sheets

METHOD FOR ANALYZING SECRETOME, BIOMARKER FOR LUNG CANCER METASTASIS, AND SIRNA COMPOUND FOR INHIBITING LUNG CANCER METASTASIS

CROSS REFERENCE TO RELATED APPLICATION

This application claims the benefits of the Taiwan Patent Application Serial Number 100114124, filed on Apr. 22, 2011, the subject matter of which is incorporated herein by reference.

BACKGROUND OF THE INVENTION

1. Field of the Invention

The present invention relates to a method for analyzing secretome, a biomarker for lung cancer metastasis, and a siRNA compound for inhibiting lung cancer metastasis and, more particularly, to a method for analyzing secretome related with cancers, a biomarker for lung cancer metastasis obtained from the aforementioned method, and a siRNA compound for inhibiting lung cancer metastasis which is developed from the aforementioned biomarker.

2. Description of Related Art

Cancer metastasis is a very complicated process, and is a main causal factor in cancer deaths. During the process of cancer metastasis, tumor cells are first separated from original foci and subsequently invade into peripheral blood vessels or lymphatic vessels. Then, the separated tumor cells transfer to other organs through the circulatory system or lymphatic system, and develop tumor cells on other organs.

Many studies have found that secretome plays an important role in inducing tumor cell migration and invasion during the cancer metastasis process, and increases the probability that cancer cells migrate to other organs though an extracellular matrix. Hence, if the proteins from the secretome related to the cancer metastasis can be identified, the obtained proteins can be used to evaluate the risk of cancer metastasis and potentially inhibit cancer metastasis.

Recently, many secretome analytic methods have been developed to analyze the proteome secreted from cells. These methods are performed by purifying secretome, and analyzing the purified secretome with LC-MS/MS. However, there are high-concentrated salts and many contaminants contained in the secretome sample, and the matrix in the medium may influence the results of sequential mass spectrometry analysis.

In addition, many exosomes, glycoproteins and transmembrane proteins are contained in the secretome. These proteins are hard to separate or digest, and may influence the results of analysis. Even though these proteins can be separated or digested, the chemical compound in the reagent for separation or digestion may also deteriorate the liquid chromatography system. Hence, there are no effective methods to effectively analyze secretome from cells.

Secretome is highly related to cancer metastasis. Furthermore, if an effective method for analyzing secretome can be developed, proteins related to cancer metastasis can be identified through this method, and the identified proteins can further be applied in evaluation or inhibition of cancer metastasis.

The mortality (death rate) from lung cancer is among the highest of all cancers, and the risk of suffering from lung cancer in Taiwan is higher than other countries. According to the data published by Department of Health in Taiwan, lung cancer is the most common cause of local cancer-related death. Hence, if the proteins related to lung cancer metastasis can be identified from secretome, the mortality from lung cancer may further be reduced.

SUMMARY OF THE INVENTION

The object of the present invention is to provide a method to analyze various proteins in secretome.

Another object of the present invention is to provide a biomarker for lung cancer metastasis, which can be used to evaluate the risk of lung cancer metastasis and reduce the mortality from lung cancer.

A further object of the present invention is to provide a siRNA compound for inhibiting lung cancer metastasis, which can be applied to lung cancer gene therapy.

To achieve the objects, the method for analyzing secretome of the present invention comprises the following steps: (A) collecting proteome secreted from a cell; (B) providing a purification gel, wherein the purification gel comprises a low-density layer and a high-density layer, with the low-density layer stacked on the high-density layer; (C) adding the proteome on the low-density layer and separating the proteome through the low-density layer and the high-density layer of the purification gel; (D) collecting a separated proteome on an interface between the low-density layer and the high-density layer, and tagging the separated proteome with a reagent after a digestion process; and (E) analyzing the separated proteome tagged with the reagent and comparing an analysis result of the separated proteome with a proteomic database. Herein, the digestion process means to digest the separated proteome with a peptide mixture being obtained after the separated proteome is digested.

According to the method for analyzing secretome of the present invention, the proteome secreted from cells can be easily purified by using the purification gel with two density layers. In addition, a reagent is used to tag proteins in the method of the present invention so that not only can the types of proteins in the secretome be analyzed, but the quantity of the proteins can also be obtained. In the last step (E) of the method of the present invention, the obtained analysis result of the separated proteome is compared with a proteomic database to identify the proteins in the separated proteome and do follow-up studies. For example, the proteins obtained by the comparison with the proteomic database is further quantified with the signal of the tagged reagent, allowing the secretome related to cancer metastasis to be found based on the quantification results. Hence, the present invention provides a simple and quick method for analyzing secretome, which can be used to identify the types of proteins in the proteome secreted by cells. In addition, the quantification analysis can be used to find the secretome with expression differences, which can be applied to detect the proteins related to cancer metastasis.

According to the method for analyzing secretome of the present invention, the content of polyacrylamide in the low-density layer is lower than that in the high-density layer. Preferably, the low-density layer comprises 3-6 wt % of polyacrylamide, and the high-density layer comprises 10-25 wt % of polyacrylamide. More preferably, the low-density layer comprises 3-5 wt % of polyacrylamide, and the high-density layer comprises 15-25 wt % of polyacrylamide. Most preferably, the low-density layer comprises about 4 wt % of polyacrylamide, and the high-density layer comprises about 20 wt % of polyacrylamide.

In addition, according to the method for analyzing secretome of the present invention, the reagent can be any isotope reagent generally used in the art. For example, the reagent can be protein/peptide labeling, metabolic labeling, or enzymatic labeling. Herein, the protein/peptide labeling can be Isotope Coded Affinity Tags (ICAT), or Isobaric Tags for Relative and Absolute Quantitation (iTRAQ), and the metabolic labeling can be Stable Isotope Labeling with Amino Acids in Cell Culture (SILAC). In the method of the present invention, the isotope reagent is iTRAQ, which is an isotope reagent tagged on the amino functional groups such as the N-terminal of a peptide or amino acids with amino functional groups. In addition, the signal emitting from the isotope reagents can be used to quantify the amount of tagged proteins or peptides.

In step (E) of the method for analyzing secretome of the present invention, the separated proteome tagged with the reagent is analyzed with a liquid chromatography-mass spectrometer. Preferably, the separated proteome tagged with the reagent is analyzed with LC-MS/MS.

According to the method for analyzing secretome of the present invention, the types of the secretome are not particularly limited. Preferably, the secretome is proteome secreted from tumor cells. More preferably, the secretome is proteome secreted from lung cancer cells.

When the aforementioned method for analyzing secretome of the present invention is performed to analyze the secretome from lung cancer cells, proteins highly related to lung cancer metastasis and/or invasion can be found. Hence, the present invention further provides a biomarker for lung cancer metastasis and/or invasion, which is selected from the group consisting of a nucleotide sequence, a complementary sequence of the nucleotide sequence, a derivative of the nucleotide sequence, an amino-acid sequence, a derivative of the amino-acid sequence, a fragment of the amino-acid sequence, a mutation of the amino-acid sequence, and an antibody corresponding to the amino-acid sequence of a metastasis and/or invasion protein of lung cancer. Herein, the metastasis and/or invasion protein of lung cancer can be selected from the group consisting of TIMP1, PRDX 1, uPA, AAT, and COL6A 1. Hence, the risk of lung cancer metastasis can be evaluated by detecting the contents of the biomarker for lung cancer metastasis and/or invasion in lung cancer patients, and particularly the contents of the aforementioned metastasis and/or invasion proteins. Therefore, the mortality rate for lung cancer patients can be reduced. In addition, the biomarker for lung cancer metastasis and/or invasion can further be applied to clinical prediction of cancer metastasis or the development of a prognostic index and target therapy.

According to the biomarker for lung cancer metastasis and/or invasion of the present invention, preferably, the metastasis and/or invasion protein of lung cancer is recognized as COL6A1 (Collagen alpha-1 (VI) chain), wherein the nucleotide sequence (DNA sequence) of COL6A1 is represented by SEQ ID NO: 1, and the amino-acid sequence (protein sequence) of COL6A1 is represented by SEQ ID NO: 2.

Furthermore, the present invention also provides a siRNA compound for inhibiting lung cancer metastasis and/or invasion which comprises a target sequence selected from the gene of COL6A1. When the siRNA of the present invention is applied on RNA interference gene therapy, the probability of lung cancer metastasis and/or invasion can be inhibited, and the mortality rate for lung cancer can further be reduced.

According to the siRNA compound for inhibiting lung cancer metastasis and/or invasion of the present invention, the target sequence comprises 20-25 continuous nucleotides randomly selected from the nucleotide sequence (DNA sequence) or the complementary sequence of the nucleotide sequence of COL6A1. Preferably, the nucleotide sequence of COL6A1 is represented by SEQ ID NO: 1. In addition, the target sequence is preferably, at least one selected from the sequences represented by SEQ ID NO: 3, SEQ ID NO: 4, SEQ ID NO: 5, SEQ ID NO: 6, SEQ ID NO: 7, and SEQ ID NO: 8, or a combination containing at least two selected therefrom.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
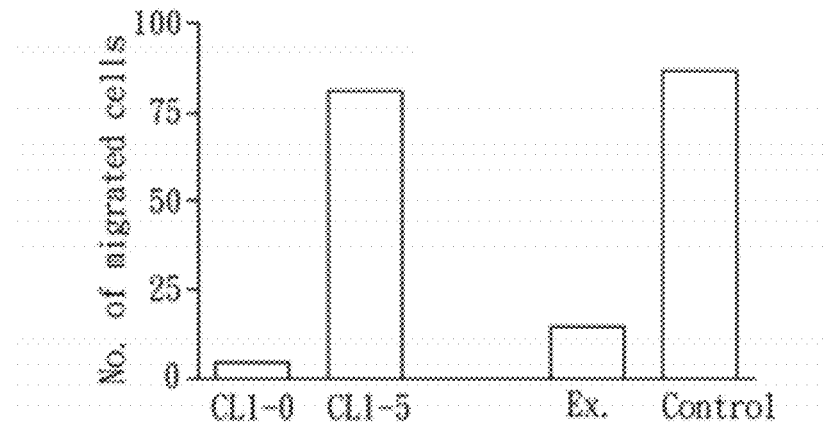
FIG. 1 is a result of migration assay showing the migration capability of cells transfected with COL6A 1 siRNA according to an embodiment of the present invention.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Lung Cancer Cell Line CL1

In the present embodiment, lung cancer cell lines (CL1-0 and CL1-5 cells) with different invasive and metastatic capabilities were provided by Dr. P. C. Yang (Department of Internal Medicine, National Taiwan University Hospital, Taipei, Taiwan, Republic of China). The cells were maintained in an RPMI 1640 medium supplemented with 10% fetal bovine serum (FBS) and antibiotics at 37° C. under 5% $CO_2$.

Harvest of Conditioned Media from Lung Cancer Cell Lines

CL1 cells were grown to confluence in tissue culture dishes, washed with serum-free media three times to avoid serum contamination, and incubated in serum-free media for 24 h. The supernatants of the conditioned media (CM) were then harvested and centrifuged to eliminate the intact cells and contaminants. Next, the supernatants were concentrated and desalted by centrifugation in Amicon Ultra-15 tubes (molecular weight cutoff 3000 Da; Millipore, Billerica, Mass.). The protein concentrations of CL1 CM samples were determined using the Bradford protein assay reagent (Biorad). Herein, the protein concentrations obtained by Bradford protein assay reagent were the concentrations of secretome.

Separation and Purification of Secretome

The obtained secretome from concentrated CM samples was purified with a purification gel. Herein, the purification gel was prepared as follows. First, 0.6 mL of $H_2O$, 2.22 mL of 1.5M Tris-HCl [pH 8.8], 90 μL of 10% SDS, 6 mL of Bis/Acrylamide, 90 μL of 10% ammonium persulfate, and 5 μL of TEMED were mixed well and set to polymerize for 1 hour to obtain a resolving gel portion (i.e. high-density layer). Then, 2.9 mL of $H_2O$, 0.5 mL of 1 M Tris-HCl [pH 6.8], 40 μL of 10% SDS, 520 μL of Bis/Acrylamide, 40 μL of 10% ammonium persulfate, and 4 μL of TEMED were mixed and poured on the resolving gel portion. After a setting process was performed for 30 mins, a stacking gel portion (i.e. low-density layer) was obtained. After the aforementioned process, a purification gel was obtained, which comprises a resolving gel portion (i.e. high-density layer) and a stacking gel portion (i.e. low-density layer). In addition, the low-density layer was stacked on the high-density layer.

A total of 100 μg of secretome was mixed with 13 μL of $H_2O$, 5 μL of 4×SDS sample buffer, and 2 μL of 0.5M DTT and then boiled under 95° C. for 10 min. The purification was run at 55 V. The electrophoresis was stopped after the sample had just passed into the resolving gel portion, and the gels were then stained using Coomassie Brilliant Blue (CBB) R-250.

In-Gel Digestion

The secretome sample located on an interface between the low-density layer and the high-density layer was collected and the gel pieces were diced into about 1 mm³ Gel slices were washed and dehydrated three times in 25 mM ammonium bicarbonate (ABC) (pH 7.9) and 50 mM ABC/50% acetonitrile. A protein reduction was subsequently performed by incubating 0.5M DTT for 1 h at 56° C. and then alkylating with 50 μL saturated IAA for 45 min at room temperature in the dark. After two subsequent wash/dehydration cycles, each gel sample was digested with 4 μg (1:25, w/w) of sequencing-grade modified trypsin (Promega)/25 mM ammonium bicarbonate and incubated at 37° C. for an overnight digestion (16-18 hours). After the digestion process, peptides, which were obtained from the secretome, were extracted twice in 100 μL of 50% ACN in 5% formic acid. The extracted peptides were enriched using OMIX C18 pipet tips (Varian) to remove any contaminants, which may have affected the signal of the sequential iTRAQ labeling.

Isotope Labeling of Peptides from Secretome

The enriched peptides from the secretome were labeled with the iTRAQ reagent (Applied Biosystems, Foster City, Calif., USA) according to the manufacturer's protocol.

Briefly, one unit of iTRAQ reagent was thawed and reconstituted in ethanol (70 μL), wherein one unit was defined as the amount of reagent required to record 100 μg of protein. The obtained peptide mixtures were reconstituted with 20 μL of iTRAQ dissolution buffer. 70 μL iTRAQ reagent solutions (iTRAQ 115: iTRAQ 116=1:1, or iTRAQ 114: iTRAQ 117=1:1) were combined with the peptide mixtures from the secretomes. The extracted peptide mixtures were then pooled and dried by vacuum centrifugation. The dried peptide mixture was reconstituted and acidified with 10 μL of buffer (5 mM $K_2HPO_4$ and 25% ACN [pH 3]) for fractionation by SCX chromatography using an AKTA FPLC system (GE Healthcare) to reduce the complication of the samples. A total of 28 fractionations were generated and were desalted using OMIX C18 pipet tips (Varian) according to the user instructions in order to remove the salts which may influence the signal of isotope reagents.

Analysis of Peptides from Secretome with LC-ESI-MS/MS iTRAQ-labeled samples were reconstituted in eluent buffer A (0.1% (v/v) FA in H2O) and analyzed by LCMS/MS. The buffer B (0.1% (v/v) FA in ACN) gradient started from 0% to 5% at 2 mins and then progressed to 37% in 140 mins. Peptides were eluted at 200-300 nL/min.

Peptide fragmentation by collision-induced dissociation was performed automatically using the information-dependent acquisition in Analyst QS v1.1 (Applied Biosystems). The method applied a 1-s TOF MS scan and automatically switched to three 2-s product ion scans (MS/MS) when a target ion reached an intensity of greater than 20 counts. TOF MS scanning was undertaken over the range 400-2000 m/z. Product ion scans were undertaken over the range 100-2000 m/z at low resolution.

Database Comparison

The results from LC-MS/MS were batch-searched against the Swiss-Prot human sequence database (version 20090616; 468851 sequences) using the MASCOT algorithm (v2.1.0, Matrix Science, London, U.K.). The peak list in the MS/MS spectra generated under ESI-Q-TOF was extracted with AnalystQS 1.1 (Applied Biosystems) with the default charge state set to 2+, 3+, and 4+. The MS and MS/MS centroid parameters were set to 10% height percentage and to a merge distance of 0.1 amu. For the MS/MS grouping, the averaging parameters consisted of rejection of spectra with less than five peaks or precursor ions with less than 10 counts/s. Search parameters for peptide and for MS/MS mass tolerance were 1 and 0.5 Da, respectively, with allowance for two missed cleavages made in the trypsin digest and for variable modifications of deamidation (Asn, Gln), oxidation (Met), iTRAQ (Nterminal), iTRAQ (Lys), and carboxyamidomethylation (Cys). Peptides were considered to have been identified if their MASCOT individual ion score was higher than the MASCOT score 20.

After the aforementioned analysis, 353 proteins were identified from the secretome of lung cancer samples.

Protein Quantification

For protein quantification, data analysis for the iTRAQ experiments was performed with the software Multi-Q. The raw data files from QSTAR Pulsar I were converted into files of mzXML format by the program mzFAST, and the search results in MASCOT were exported in comma-separated-values (CSV) data format. After the data conversions, Multi-Q selected iTRAQ labeled peptides with confident MS/MS identifications (MASCOT score 20), detected signature ions (m/z 114, 115, 116, and 117), and performed an automated quantification of peptide abundance.

To calculate the average protein ratios, the ratios of quantified, unique iTRAQ peptides were weighted according to their peak intensities to minimize standard deviation.

Bioinformatics Analysis

The identified proteins were analyzed using the SignalP, SecretomeP, and TMpred programs to predict the possibility of protein secretion through classic or through nonclassic secretion pathways and the presence of transmembrane domains in the protein sequence. The molecular functions of the identified proteins were determined based on a search against the Human Protein Reference Database (HPRD) (http://www.hprd.org/).

After the bioinformatics analysis, more than 83% of identified proteins may be assumed to be secreted proteins through different secretion pathways.

In addition, after the aforementioned analysis, three and four proteins were respectively selected from CL1-0 and CL1-5 cell lines, which were related to lung cancer metastasis. From the CL1-0 cell lines, the three proteins were retinal dehydrogenase 1 (AL1A1), nidogen-1 (NID-1), and peroxiredoxin-1 (PRDX1). From the CL1-5 cell lines, the four proteins were collagen alpha-1 (VI) chain (COL6A1), metalloprotease inhibitor 1 (TIMP 1), urokinase-type plasminogen activator (uPA), and alpha-1-antitrypsin (AAT).

Western Blotting Analysis

The aforementioned seven proteins related to lung cancer metastasis, which includes PRDX1, NID, AL1A1, COL6A1, uPA, TIM1, AAT were examined through western blotting analysis, in order to identify whether these proteins were indeed related to lung cancer metastasis.

First, 5-30 μg of secreted proteins from the CL1 cell CMs were separated on a 12% SDS-PAGE and transferred to PVDF membranes (Millipore). The membranes were blocked in a 5% nonfat milk solution for 1 hour at room temperature and then probed with various antibodies against the selected proteins (Santa Cruz Biotechnology) and against anti-α-tubulin (Calbiochem) for 3 hours. The membranes were then washed three times with TBST and incubated with secondary antibody in TBST/2% skim milk for 50 mins. Bound antibody was detected using the Enhanced Chemiluminescence System. Chemiluminescent signals were captured using the Fujifilm LAS 3000 system (Fujifilm).

The results of western blotting analysis show that the expression of TIMP1, COL6A1, uPA and AAT can be identified in the CL1-5 with high invasive capacity and the expression of PRDX1 and NID-1 can be identified in the CL1-0 with low invasive capacity. Hence, according to the results of western blotting analysis, the proteins highly related to lung cancer metastasis can be identified through the aforementioned gel purification, isotope labeling, and mass spectrometry of the present embodiment.

siRNA Interference

There are no studies showing that COL6A1 is related to cancer metastasis. Herein, COL6A1 gene silencing was performed to identify the relation between COL6A1 and cancer metastasis.

In the present analysis, COL6A1 siRNA was provided, which was a mixture containing DNA sequences represented by SEQ ID NO: 3, SEQ ID NO: 4, SEQ ID NO: 5, SEQ ID NO: 6, SEQ ID NO: 7 and SEQ ID NO: 8. Then, CL1-5 cells were transfected with COL6A1 siRNAs using the siRNA transfection reagent according to the manufacturer's instructions (Santa Cruz Biotechnology, Santa Cruz, Calif.). For each transfection, 0.5 μg of COL6A1 siRNA or control siRNA (scramble siRNA) with 4 μL of siRNA transfection reagent was added to 100 μL of siRNA transfection media. The solution was mixed gently and overlaid onto the CL1-5 cells for 24 h. The media was then aspirated and $2\times10^5$ CL1-5 cells were grown in RPMI 1640 containing 10% fetal bovine serum (FBS) on six-well culture dishes reaching 80% confluence at 37° C. under 5% $CO_2$. Herein, the experimental group (Ex.) was CL1-5 cells transfected with COL6A1 siRNA, and the control group (Control) was CL1-5 cells transfected with scramble siRNA. Then, the aforementioned western blotting analysis was performed to identify the results of siRNA interference. In addition, the CL1-5 cells transfected with COL6A1 siRNA were further used to perform the following wound healing assay, migration assay and matrigel invasion assay.

The results of siRNA interference show that the transfection of COL6A1 siRNA can inhibit the protein expression of COL6A1 in CL1-5 cells. Hence, the COL6A1 siRNAs used in the present embodiment has effect on inhibiting the expression of COL6A1 protein.

Over-Expression of COL6A1 Protein $2\times10^5$ CL1-0 cells were grown in RPMI 1640 containing 10% fetal bovine serum (FBS) on six-well culture dishes reaching 70% confluence. CL1-0 cells were then grown in RPMI 1640 media and transfected with plasmids containing COL6A1 and the empty vectors. For each overexpression transfection experiment, 200 μL of RPMI 1640 serum-free medium containing 4 μL of transfection reagent (TurboFect, Fermentas) mixed with 2 μg of plasmid was added to the CL1-0 cells for 24 hours incubation. Transfection efficiency was monitored by the aforementioned western blotting analysis. Herein, the experimental group (Ex.) was CL1-0 cell transfected with plasmids containing COL6A1 vectors, and the control group (Control) was CL1-0 cell transfected plasmids containing empty vectors.

The results show that COL6A1 proteins over-expressed not only inside the CL1-0 cells, but also in CM. In addition, the CL1-0 cells transfected with plasmids containing COL6A1 and the empty vectors were used to perform the following wound healing assay, migration assay and matrigel invasion assay.

Wound-Healing Assay

CL1 cells were seeded in precision-molded inserts (Ibidi, Martinsried, Germany) that created a defined wound gap to monitor cell migration and grown in the RPMI 1640 medium containing 10% FBS according to manufacturer's protocol. Cells were allowed to close the wound for 24 hours. Images were taken at 100× magnification, and photographs were taken at 0 and 24 hour at the same position in the wound. The areas of the cell-free zone into which cells migrated (based on the zero line of the linear "wound") were quantified under the microscope using Image-Pro Plus software (Version 6.0).

The results show that CL1-5 cells exhibited a higher invasive capability than CL1-0 cells. In addition, COL6A1 siRNA led to a dramatic decrease of invasion in the COL6A1-siRNA-transfected CL1-5 cells. These results demonstrate that the knock-down of COL6A1 expression impairs migration and invasion in CL1-5 cells and that COL6A1 is critical for migration and invasion in CL1-5 cells. On the other hand, CL1-0 cell transfected with plasmids containing COL6A1 vectors exhibited increased migration capability due to the increased protein expression of COL6A1.

Migration Assay

A transwell membrane (8-μm pore size, BD Biosciences) was used for a transwell migration assay, The CL1 cells were trypsinized, washed, and kept suspended in their medium without FBS. To the lower wells of the chambers, a migration inducing medium (with 10% FBS) was added. The upper wells were filled with a serum-free medium with cells (10,000 cells per well), and the lower chambers were filled with an RPMI 1640 medium supplemented with 10% FBS to induce cell migration. After 8 hours, the assays were stopped by the removal of the medium from the upper wells and the careful removal of the filters. The filters were fixed with methanol and then stained with 20% Giemsa solution (Sigma). The cell number on each filter was counted under a microscope (200×).

Figure 2:
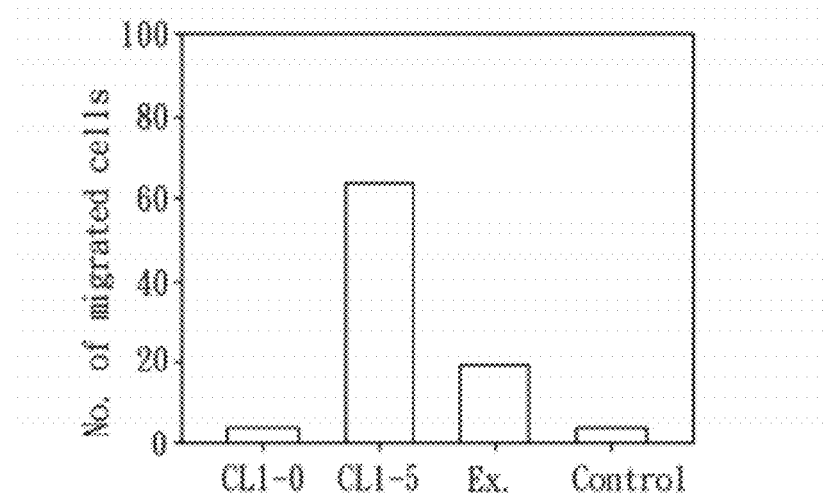
FIG. 2 is a result of migration assay showing the migration capability of cells with over-expressed COL6A1 protein according to an embodiment of the present invention.

As shown in FIG. 1, a decrease in migration was observed in the COL6A1-siRNA-transfected CL1-5 cells (experimental group, Ex.) in comparison with the normal and control CL1-5 cells (control group, Control). The RNA slicing interferes the protein expression of COL6A1, so the migration capability of cells is greatly decreased. In addition, as shown in FIG. 2, CL1-0 cells transfected with plasmids containing COL6A1 has increased migration capability, due to the increase of COL6A1 protein expression.

Matrigel Invasion Assay

Cell invasion was examined in a membrane invasion culture system. A transwell membrane (8-μm pore size, BD Biosciences) coated with Matrigel basement membrane matrix (2.5 mg/mL; BD Biosciences Discovery Labware) was used for the invasion assay. Cells ($1\times10^5$) were seeded into the upper wells in an RPMI 1640 medium, and the lower chambers were filled with an RPMI 1640 medium supplemented with 10% FBS. After incubating at 37° C. for 24 h, cells on the upper side of the filter membrane were gently removed with cotton swabs. The number of cells migrating through the membrane to the lower side was determined by fixing the membranes with methanol and staining the cells with propidium iodide. The cell number on each filter was counted in five randomly selected fields under a microscope (200×).

Figure 3:
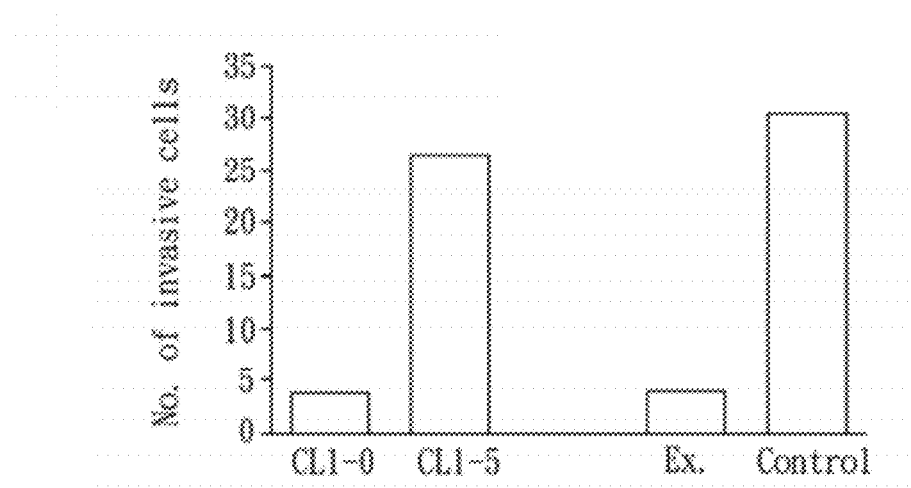
FIG. 3 is a result of migration assay showing the invasive capability of cells transfected with COL6A1 siRNA according to an embodiment of the present invention.
Figure 4:
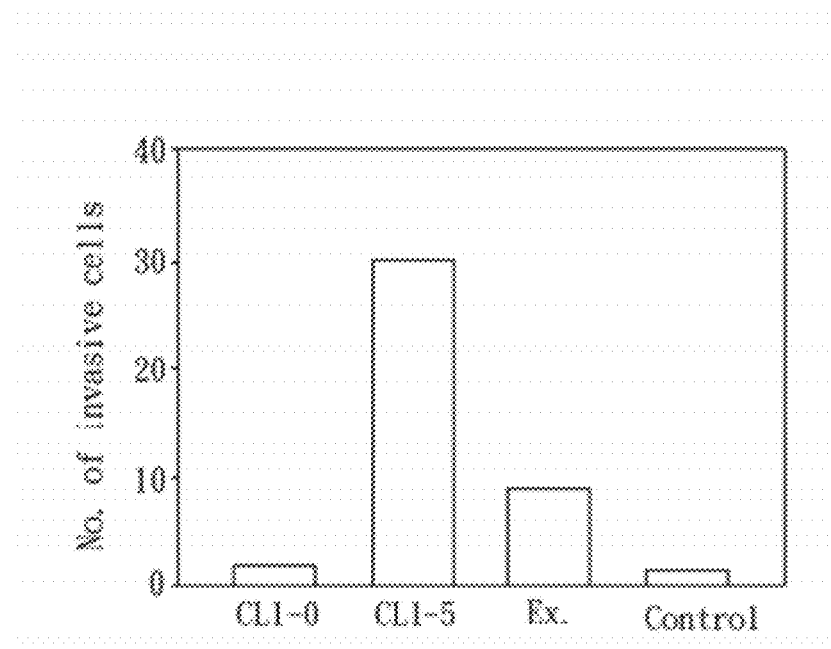
FIG. 4 is a result of migration assay showing the invasive capability of cells with over-expressed COL6A1 protein according to an embodiment of the present invention.

The results show that the invasive capability of CL1-5 cells is higher than that of CL1-0 cell. In addition, a decrease in invasion was observed in the COL6A1-siRNA-transfected CL1-5 cells (experimental group, Ex.) in comparison with the normal and control CL1-5 cells (control group, Control), as shown in FIG. 3. The RNA slicing interferes the protein expression of COL6A1, so the invasive capability of cells is greatly decreased. In addition, as shown in FIG. 4, CL1-0 cells transfected with plasmids containing COL6A1 has increased invasive capability, due to the increase of COL6A1 protein expression, as shown in FIG. 4.

According to the results of wound-healing assay, migration assay and matrigel invasion assay, the invasive and migration capability of CL1-5 cells can be reduced by inhibiting the expression of COL6A1. On the other hand, the invasive and migration capability of CL1-0 cells can be enhanced when COL6A1 is over-expressed. Hence, COL6A1 is highly related to the migration/invasion of lung cancer cells. When RNAi gene therapy is applied to inhibit the expression of COL6A1, the purpose of inhibiting lung cancer migration/invasion can be achieved.

Although the present invention has been explained in relation to its preferred embodiment, it is to be understood that many other possible modifications and variations can be made without departing from the spirit and scope of the invention as hereinafter claimed.

What is claimed is:

1. A mixture of siRNA compounds for inhibiting lung cancer metastasis, comprising:
    nucleotide sequences represented by SEQ ID NO: 3, SEQ ID NO: 4, SEQ ID NO: 5, SEQ ID NO: 6, SEQ ID NO: 7, and SEQ ID NO: 8.

2. The mixture of siRNA compounds as claimed in claim 1, wherein each of the nucleotide sequences comprise 20-25 continuous nucleotides from COL6A1.

3. The mixture of siRNA compounds as claimed in claim 2, wherein the nucleotide sequence of COL6A1 is represented by SEQ ID NO: 1.

* * * * *

SEQUENCE LISTING

<160> NUMBER OF SEQ ID NOS: 8

<210> SEQ ID NO 1
<211> LENGTH: 23314
<212> TYPE: DNA
<213> ORGANISM: Homo sapiens

<400> SEQUENCE: 1

```
tccttgccct ccgctctcac tctggctggg agcagaaggc agcctcggtc tctgggcggc       60
ggcggcggcc cactctgccc tggccgcgct gtgtggtgac cgcaggcccc agacatgagg      120
gcggcccgtg ctctgctgcc cctgctgctg caggcctgct ggacagccgc gcaggatgag      180
ccggagaccc cgagggccgt ggccttccag ggtgagtggt ggcttggggt gcaggctcca      240 gacccccgc tctttgctgc cggccagggc cagatgcgcg gggtccctc ccacgcgtgg       300 aactgcagac tgggggcctg gagcccctga acccactcc ccgctcgggg cggctgcagc      360
gcccagctct gccccaccgg gccttggccg gggccctag aggctcagca ttcagcattc      420 tcagcgggc cggaccgcag gcagctcggg aggggctccc tggcgagggg gagctggtgc      480
ggggctgtct cggcgccccg tgaatccgtt tgacccctca cctggcagtg agtccagacg      540
cacggccccc ccgaccccg ttctagaaga agtcgtgcgc tgctggttct gaatccagcg      600
agaaaccttc ccgtgaggtc tcacttgtcc ggtcccgtgc cggggacgcc ctgcccttcg      660
ggggaggttg tgaaggtttc tgactcccct cgaggcacag gagcggtttg gggtctctca      720 ctccacccc tccccaccgt ccccaccgag ggacgtcctg ctgccttttc ccgggagagc      780
ctctccgggc ccggggctct gtgctgcagg cgctgggctg gccgggaggg caggcccagc      840
agagactcgg ggaatggggc gagagcttga aggccctct cctccatctt cggccagact      900
gccccgtgga cctgttcttt gtgctggaca cctctgagag cgtggccctg aggctgaagc      960
cctacggggc cctcgtggac aaagtcaagt ccttcaccaa gcgcttcatc gacaacctga     1020
gggacaggta ggagggacgc cccgtgacct tcctcctgtg cttctgggcc tcttggaggg     1080
aggggtgggg gcccagggga acacgggtgc gacggcctca acctcctaag gttgggcgag     1140
cgttgccctg accggggccc ctcccggcgc cctccagagt gaggccgggg ccctttccgg     1200
cgccctccag agtgagctgg tctgagcctc tcccagcgcc ttccagagtg agctggtttg     1260
agaccctgct cgcgggggtg gcacctgttc agcagggccg aggtgacagt gaggctgaga     1320
tgtagggaag agaggctccc gcaggctgac cgagagggct cagcgcactg gcccagacac     1380
gcagtcctgc ctggtgcgcg ggagccctc actaaccacc tggaccctgg tttgttccgt     1440
gggcagtgag agcctctacc tgggtcctgg atcccacgtt ctgaaggtcc ccgactcggg     1500
```

-continued

```
agccaggagg ggtgtcgctc tgcagcccca gggcccccag gcttggttct gggcttggga      1560
cacggcaccc tctgctccac gttcctccat ctgtgcgtgt ggctgaggac agaccggggg      1620
gagaggggag tcggtcctgt gggtgcacag ggccgctgag ggggggggcat gtagaacggg     1680 gctcccccac tgagacgggt cctggcagtg gggacacagc ttagccggcg taggaaccccc    1740 cgtcctcctt gaccctgctg actggccgct gggccggagc ctcccgccac cagaaggggc     1800
acagtcagag gctgccggta acagcagggt ggaccttcca gcccacaccg tgcccagcag     1860
gagccattgg taccaggaac cctgagctta gtggacatgg ccaggcccgt gcggcagtgt     1920
ttgggggggg gtctggctgt ggatggcacc ggggaggggc ggccgcgtgg cccagcgtcc    1980
cccgagtcgc ccttgttgcc tttactcagt ctccccatga ctcagtttcc cacctgtgaa     2040
atggggcgga gtcatcccca tgtcgctgcc actggattcc tgcaggcgcc gtggtcactc     2100
tgctgaatgg atgggagggt gggtggggca gaggtgggcc caccccaggc tggggcagag     2160
cagacccctg agagcctcag gctcaggtgc tcagagggca gcgaggggggc tgctcagatc     2220 cccggggtgc ctccttcccc cactgtcatg ctgcccact gcaggcccaa ggaccccacc      2280
ccagcagggc cacacactca gggctcctgg tctgagggcc tgagggatcg gggcgcaggt     2340
cgcttgctgg ccacacccgc ctgcacagcc ttccaggagg gccggcctca gggccacagg     2400
gcaagtccag ctgtgtgtca gccacggcca gggtggggca gcctgtccat ctgggtgacg     2460
tcgcgccctg ggacgggtag cgatggcgcc aggggccgcc cgcctcacgc cgccgtgcc     2520 tgttcctggc aggtactacc gctgtgaccg aaacctggtg tggaacgcag gcgcgctgca     2580
ctacagtgac gaggtggaga tcatccaagg cctcacgcgc atgcctggcg gccgcgacgc     2640
actcaaaagc agcgtggacg cggtcaagta ctttgggaag ggcacctaca ccgactgcgc    2700
tatcaagaag gggctggagc agctcctcgt ggggtgagtg gccccagcc tcctgcccac      2760 gccagttctc acgcgtggta cccagcctgg gctggggttg gcctggggtc cctgtgcggc     2820
ttcagctgca gcctccctgt tctcttggag gctgcacggc ctccctgacc cactttgtgg     2880
gcaggaaaga gacggagaca gacagagaca gagagaaaca gaaacaggga gaaacagaca     2940
cagagagaga cagagacaga gagagataga gacagagaca gagagagaca gagacaaaga    3000
gtgacagagg gaccaagaca ggcagacaga gacaaacaga gacagagaca gagacacaga    3060
gagagacaca gagagacaga gacgggaaca gagacaggca gacagagaca gagagagaca    3120
gagacagaaa cagagacaga gggacagaga caggcagaga gagacagaga gacagagaca    3180
gagacagaca aacagagaca gagagacaga aacagggaca gagacagaaa gagagagaga    3240
cagagggaaa cagagagaga cagagacaga tagaaaaaga cagaggcaga gagaagcaga    3300
gacagagaaa caaagacagt cagagacaga cagagacaga gacagaaaca gagacagaga    3360
gacagagaca gagggcaga gacaggcaga cagagagaca gagacagaga cagcgaaaca    3420
gagacagaaa catacagaga cagagagaca gagagaagca gagacagaca gaggcagaga    3480
gacagagaga agcagagaca gggacagaga cagagacaga aatagagaga tagagacaga    3540
gggacagaga cagagagata gagacagaga gggacagaga gagatagaag cagagagaga    3600
gagacaaaga cagaggcaga gagacagaga gagaagcaca gacagagaca gacagagaga    3660
cagggacaga cagagacaga gagaccggaa acagaggcag agagactgag agactgagag    3720
agacggggtg gttttcccca cagcatcaac accaagcagg gctaggatca ctgaaacaga    3780
ctcatcagac ccgaagcatg cgctttctcg gggttttttct ggactgaggg gtttcctctc    3840
atcccagtgt ccagctgtgg ggacgcaggg gccgcaagcc ccggagtgtc cagaggggaa    3900
```

```
cgtggcctcc ccacacccag cccttcacga ggcctcagga tcccagtggg ggtacccgag    3960
gctgccctgt ccagccaggc ggtgcggggg gtttggggag agcctctccc cgaggtcggt    4020
ctcagagggc cacatggccg gtgtgggccg gacattccct ttccaatggt tgtgcccact    4080
tccctccaga gttggtgcca agctgggacc tgggggactt ggagtctcag gaagtcgtcc    4140
gctgtctgca gggggtgcat gggggatgtg ccacacacg tcagagtgcg gcccctgtg     4200 gaagccacag acagacacga ctcccctaaa tgagctcgcc cttctggccg agatgctcag    4260
cgtccccagc aggctgcccg actgccctgc gatactgccc tccttcctgc tgctcccact    4320
ttccctttcg gggggttgga tttggggcat tcagggatcg ccctgttgtt tgctcatcac    4380
acccatttcc tgcaagagcc acggtgaccg agcagccttg agttgaggca gcttgtgggt    4440
agacgcggcg ggcatctcgg aggggcacgc tccctgccac cctcagcctc cactcactgg    4500
tcagggcctt tgcgccccag ggcaccccag gaaccgagcc tcctttgggg tcatgggtgc    4560
ctctcctggg agggcgtgga ttttccaaag cagtttagag aaatgagacc cacaggcgtt    4620
atttcccatg gtgaggttct tttcagtaac ccccaccgta tagccaggat cagcaaagag    4680
aggcggctcc tcccggtgag acagggacca gcacctcccg gacaggcttg ggtctccctc    4740
cagttccccc acctagtctc gaggtctcac gctgccctct cctgtccagg ggctcccacc    4800
tgaaggagaa taagtacctg attgtggtga ccgacgggca ccccctggag ggctacaagg    4860
aaccctgtgg ggggctggag gatgctgtga acgaggccaa gcacctgggc gtcaaagtct    4920
tctcggtggc catcacaccc gaccacctgg taggcaccgg ccccccccgg cagatgcccc    4980
caaccacagg gagtggcggc tgcaaggccc ccggcagctg ggaccgtctt ttggtcctcg    5040
ggagggtgtg ggttctccag ccggccaccc ttgcccctga gaggccagcc cctcctgctg    5100
aggagcctgg agcgccccag cccagcctcc cctctggccc tgtgggaagc ggccccggcc    5160
gtcaggggtc ccagccctgc tcagcccacc ctgaacactg cccccaggag ccgcgtctga    5220
gcatcatcgc cacggaccac acgtaccggc gcaacttcac ggcggctgac tggggccaga    5280
gccgcgacgc agaggaggcc atcagccaga ccatcgacac catcgtggac atgatcgtga    5340
ggcccctgcc caggagacgg ggaggcccgc ggcggccgca ggtggaaagt aattctgcgt    5400
ttccatttct cttttccagaa aaataacgtg gagcaagtgg taagagccct ccccaccacc    5460
cccagccgtg agtctgcaca cgtccaccca cacgtccacc tgtgtgttca ggacgcatgt    5520
ccctatgcat atccgcccat gtgcccggga cacatgtccc ctgcgtgtct gcccgtgtgc    5580
ccgggatgtg tgtcccctg cgtgtccacc tgtgtgtctg cccatgtgcc tgggacatgt    5640
gtccgcctgt gcgtccatcc gtgtgtccgt ctgcccatgt gcctgggtcg catgtcaccc    5700
tgtgtcccag ccgtatgtcc gtggctttcc cactgactcg tctccatgct ttcccccac    5760 agtgctgctc cttcgaatgc caggtgagtg tgcccccga ccctgaccc cgcgccctgc    5820 accctgggaa cctgagtctg gggtcctggc tgaccgtccc ctctgccttg cagcctgcaa    5880
gaggacctcc ggggctccgg ggcgaccccg gctttgaggt gagtggtgac tcctgctcct    5940
cccatgtgtt gtggggcctg ggagtgggg tggcaggacc aaagcctcct gggcacccaa    6000
gtccaccatg aggatccaga ggggacggcg ggggtccaga tggagggac ggcggggtc    6060 cagatggagg ggacggcggg agtccagatg gaggggatgg cggggtccag atggaggga    6120 cggcggggtc cagatggagg ggacggcggg gtccagatgg aggggatggc ggggtccaga    6180 tggagggac ggcggggtcc agatggaggg gacggcgggg tccagatgga ggggacgtcg    6240
```

```
gggctccaga tggaggggac ggcgggagtc cagatggagg ggacggcggg gtccagatgg      6300
aggggacggc ggggtccaga tggaggggac ggcggggtcc agatggaggg gacgtcgggg      6360
ctccagatgg aggggacggc gggagtccag atggagggga cggcgtggtc cagatggagg      6420
ggacggcggg gtccagatgg aggggacgtc ggggctccag atggagggga cggcgggggt      6480
ccagatggag gggacggcgg ggtccagatg aggggacgg cggggtccag atggagggga      6540
cggcggggtc cagatggagg ggacggcggg gtccagatgg aggggacggc ggggtccaga      6600
tggaggggac ggcgggagtc cagatggagg ggacggcgtg gtccagatgg aggggacggc      6660
ggggtccaga tggaggggac gtcggggctc cagatggagg ggacggcggg gtccagatgg      6720
aggggatgtc ggggtccaga tggaagggac ggcggggtcc agcaggcagg ctccggccgt      6780
gcagggtgtg gactgtcccg ggggcgctgg gggcttctga gggtgtctct gtccgccctg      6840
ccctcagccg cactctgttc agaaggacct ttctggaggt aggagggtga gaatgtgggt      6900
cccctgcttc tgtgtggctc acataggatg accttaaacg ttagaattag ctgctgataa      6960
ttaaaacttg ccatgaggct gctcatggac ctcagatttc tggcttctcc taaaaaccat      7020
caaacccagc agctgtgggc ccgagtccca tggccatttc ctgggggtcg agctgtgacc      7080 ctgggggggct tctgtgctgc acgtccctcc cacctgtgcc tggggggtcag caaagccgag      7140 cagacaggaa cgaaggcagg gagtgggggg agctggcgtg cgggttggag ctcccagacc      7200
caggctgacc agatgtgatg gggaaggtgc tttaaagccc ttgatccctg aaggctggat      7260
gaagcgtctt tttaaaaacc tgtttcgtga ccagctttt tagaaagaaa cggggctgcc      7320
ccaaccttga cctgttttgt gttccaggga gaacgaggca agccggggct cccaggagag      7380
aagggagaag ccggagatcc tgtgagtgcc tgactgtggg gtgggggccc taagaagctg      7440
gaggcgggga acgactaggc ctcggaaact tccggaagag tggctgggtt ctgagtgcca      7500
aagtcacact gcctgttcct tgtgggtggg agcagacctg gaggggccac agcccagcca      7560
tccttccaca cagccccccca ggcagcccgt aagcccccct gccagggagg ggctgggtgg      7620
ggaggtggcc cagggtgctc aggccggcac cgtccggggc ccctgccgtg gctccttggc      7680
ccaaatccta tccatagact tccctccccc agctccacct tggagggcct cggcaccatg      7740
ggccccgtgc agcagggccc ctctctcggc ctgaccaggc ctgggctgga gggaggggtg      7800
tggggctggg tgggactggc ccctgccct gctcctccgg gggtgtctca ccatctcctc      7860
ctgtgttcca gggaagaccc ggggacctcg gacctgttgg gtaccaggga atgaaggtac      7920 gtgcccccc tttcctggcc cgagcccggt ggtgccctca gccttgcaca gcactaacaa      7980
gccttcctct tcctcttctt ccgctgggtg tgtagggaga aaagggagc cgtggggaga      8040 aggtgagtga ggctcgacct cggagctggt ctctccaggc gcagatgtgc catcctggac      8100
gagggtgtcc ccggggatga ggacagtgtc cctgacagga gaccacgtgt cctgcagacc      8160
cgctccaccg cccctcgccg tccctccat ctggaaggac aaggacagcc acccaggcac      8220
ccagcaaagg cgcctgtgtc actttcaccc caccccagag caggggtccc ccgggcggtt      8280
accctctgcg gagccggggg tcccccgggc ggttaccctc tgcggagccg ggggtccccc      8340
gggcggttac cctctgcaga gcggcccctc cccatcactg tcagtcccca tgattctcag      8400
cagtgatgtt gtcccctcgg gttggggggca cccaagcccc tgcctcgcgt gggcctaagc      8460
caggcttgcc ctgccctccc caccccaaat acccctcac accgcttcc tgtctccgca      8520 gggctccagg gacccaagg gctacaaggt gagcgtgggc tgctgggagg ggggagttct      8580 gccccacgg cagcatgtct gacctgcatc tgactcctgc cttcgttttc ccgcctcaca      8640
```

```
gggagagaag ggcaagcgtg gcatcgacgg ggtggacggc gtgaaggtga ctgggggag     8700
ataggatgga cggggaggga cgaggaggaa tggggcgaga tggggaggga cggagtggac    8760
ggcgtgaagg tgacccgggg agggatgggg tggacagtgt gaaggtgacc aggggaagga    8820
cggggaggga cggggaggga tggggtgagg tgatcccggc aggagggaca gggaggagtg    8880
gggtggacgg tgtgaaggtg accccagggg ggtgtctgct aggcagggct ttccagggag    8940
ggtgtggagg gcatggaggg caccaagtct gacagttgat tggcctcagt ttacccactt    9000
ggccgtcaga ttttctagtt ttcttcctct ttccaggggg agatggggta cccaggcctg    9060
ccaggctgca agggctcgcc cgggtttgac gtaagtcact tcctctcact gatactttaa    9120
aactagcgct gtcagcagca cctcgtgtgg accgttttga cttctgtctg ggcggtctgg    9180
ggctgctgcc agaggccgcg gtggcctctg ccggtggtgt catgctgccc tcttttctcc    9240
agggcattca aggacccct ggccccaagg gagaccccgg tgcctttgga ctgaaaggag     9300
aaaaggtgag tgacttgcgg ccctggagg accagggcct tcacggttgg ccaagcgctg     9360
aattggaaac ctctcctgga agcaagtcct ggtccgagca tgtcggccac ccgtgcggcc    9420
tcagagggga ggagctggtg gaggctggag gcaggcagag gagcagcggg gacagtgccc    9480
accgtgggga cagtggccgt ggcgctcccg cccagagcct tccctgcagc ccgagggcct    9540
tcaggcctcc gccattctgt cccccgcacc tgccgctcgc tcggcacaga tgggacccca    9600
ccgcgtcact cctagcctgc gagccgcagc ccagaatggc tctcagaact gagaatgggc    9660
tgggtggcac tgagggtggc gagtgggcgg gagggtggtg agcggggggcg ggaggagggt    9720
ggtgagcggg tgggagggcg agtgggcagc gggagggcgg gagcacgagg cgggagaagg    9780
agcttttcg tctgacagct gagtctgccg ttgctggtgt tttctctgga gtttcttgt      9840
tgaagctgaa gtgttgggga agacaaaggc gaatgctgac cccaccccaa acattcccag    9900
acgagctcct agaacccagc agacggtttc caaatctcat cttcaagttc ccagattacc    9960
ctccaggccc tagatttgag tttgccaatt tgccagcctg gcaaagctgt gccttctcta   10020
atggaaacca aatcctgccc cttagacaag atgcccttg gctgggcctc acagggaaca    10080
aggttggagc attccaggag gtctttgtgc agggttgtgg atggctgagg gtgctggggg   10140
gtctgggctc agacagtgtt ggtcagaggg agtggcctga agtatgggtg agaggccctg   10200
gatgtggcct ctgatggctg cacccctggt gcacacccct gccagcgtgt gtgactcccc   10260
cggtcttccc cagggcgagc ctggagctga cggggaggcg gggagaccag ggagctcggg   10320
accatctgga gacgaggtga ggagcttcac agccccaca catgccaggt atgggcccag    10380
ggagggtcaa ggagatggag cgaccattca acccttgttc cccacagggc cagccgggag   10440
agcctgggcc cccggagag aaaggagagg cgggcgacga ggtgagtgag gctcctgac     10500
accttcctgg ggaagtgcat ggcctcagct tctgatcctc tttgctcggg gtctactcca   10560
cgtccctgag accaaatgca gtgtgtccac cagactaacg ccggcgtctg tttctcttca   10620
tcccagggga acccaggacc tgacggtgcc cccggggagc gggtgagtgg ggcaggggca   10680
gcctgcgctg ttggcctcac catgtagctg tggacgtggc ctctgcggcc cagtctggcc   10740
ctcccagcac tgagagccat ggcctcctgc ccaagacaaa tgggtttctt cacccacacg   10800
tccaggatgc ctcttcccac agtctcagag cgggtgggac ctggggaacc aggagattcc   10860
ggcctctgca accgtggggc atgcggtgga gggtggccc ctcccagggg tcctgctggg     10920
ggagtcagtc caggccaggc ctcaagcccc accccagctg ggtgtgagtt ccagcagctg   10980
```

```
aggcttctcc cctccatgtc tctccactca gggtggccct ggagagagag gaccacgggg   11040
gaccccaggc acgcggggac caagaggaga ccctgtgagt cacagttcct ggagctggga   11100
accaccccag gaaggggcag gcggaggctg gggctgggtc aggcctccag agccacagga   11160
cacatcatga agcccctgtg gcccctcaac gtggccagcc catccccacg ccgtcaggga   11220
gggcagcccc tgaagccggc gcccagccat gtgcctgatg ctgggacctg tttcatgtga   11280
aggcgttgcc cgtggacccg gtgcccactt tcccaccagg cggcttccac gtttctgcat   11340
ccgagcttgg gttcttcttt ggaataattt tccttagtta aaattcccag cgtgaggaag   11400
ttgggtcagt accccagacg ggaagctagg cctgcagggc gcctgcctgg gaaggcttga   11460
catggaaaac tcaccccaga gccgagatgc cggcggcctc agaggccacc ccccaccttc   11520
agctccgtgg accgtgggcc tcgctaggcc accccacagc ccagcctcag ggtgcagaag   11580
cacagggccc ttctctgtcc ctgtgacttg ctgggaaatc tgtgctggat gtggggcggg   11640
gcagctggca gactccgggc gtctcagtcc catccggctc agggagagcc agggcctggc   11700
gggcagagtg aaggggagag aatgccctag tgtcccagcc cgagctgcca ggcctcagag   11760
gcagcgcccc cgggtgcccc cttgtccgag aatcaagaca tgcgactgtc gtgtgctgtg   11820
acagacaggc ggggctccag cagggccaga gagctgagcc ggggcagag tcgccgccac   11880 cgagggattt ggctccccag tgggggtgg gggatttctg acctcctccc tgggagctcc   11940
ccagaagcgc acagccccg tggaggggtc gggggacgt caaagcaggg atcgtgtgac   12000
ttagtgactc agactgcctt ctaggcccac tcctctgaga tcaggatatg agactgacag   12060
ccaggcagag cccagaggaa gggccagcca cgcagctcca gcttccggc gggccacaag   12120 tccatggcta caaacacttg ccgggtccac ggagcttgct ggagaagcag ggatgcacgc   12180
agggacgcct ctggggcccc aggaggagct gccggcctcc tgaatgaaga tagccatagc   12240
cagccacgcc gatggccacg cacgtgggcc gaggaaacgc ttggcgaggc caggaagggg   12300
ctgtgcgggg agggaaggcc ggaacagccc agtgaccacc tggacagcat gctgtggctc   12360
ccagcgtgcc cgggcagcca tcctccccaa ggatggccca gctccacact cacggctcgt   12420
ttctcttcag ggtgaagctg gcccgcaggg tgatcaggga agagaaggcc ccgttggtgt   12480
ccctggagac ccggtaggaa gcgctgtggg gttgggggc gttggccaat tgggttttg   12540 ggggtagaag tgctccagca gctcacgcac tgggggtctg ttcatttccg tttgagggcc   12600
tctgtgtttc cgtagatctc gggggtgtcc ctgcgtggga gccggctgca gggggtgagg   12660
cgcggcctgg gccgggctgg tgtggattgt tgagagcagg cccagcgccc ggggggcctga   12720 cgctgagacg ctcagcccag gtggagaagc gctgtctggg ggcccatccg gggcaagggt   12780
gcctcacagt gaggaagagg tgttggagcc cctgggagac actgggagct tggtcagcat   12840
ctgtttttct gggtcaggag ccaggcatga ctgtggctgg aggtcaactg gggagtgtga   12900
ggctatggag gtttccagaa tcccaggggtg tcaggatgaa aatgcacttt catctcattc   12960
taaattccct tctccgagcc tctggaatcg ctgtgcacgc cgcacggctt tctgtctctt   13020
cccccattct gatgactgcc atgatggtgg ctccagtgtg gtgttgcccg caggctgggc   13080
tgggccgttg catcctcccg gagctcacct gccccacggg gacaggaagg cctcacacg   13140 gtcacgcccg gagacagcaa gtctgtgctc ccgagcttgt ctgcttctgt ggacaaatcg   13200
accttacggc tccatgtgcg cagctgccca cacccgagc acaaggccag accctgggca   13260
cggcagctgt ctcagacgtc cagcaagatg gggcctcaga cccagggaga tgggagaggc   13320
cgtcccagtg caagtcacat ttgtatttct gtgcacgagg tgaaatcgtg cttttgtggt   13380
```

```
gccaacgggt gttacacagc tgttaaaaat acctgtgtca tagatgagga ccagggcagg    13440
gcttggcagg cggggtctgg gccgttcgtc cacctggtcc tgcgtgccgc tcacggcagg    13500
ggcagaaagg gctcccgaca ccttcctggg gaagtgcacg gcctcagtct ctgatcctct    13560
ttgctctttg agctcccggg gctccagccc tgaggatgat ctgacctccc atgtggtcac    13620
ccaggacagg gccaggtgca gggcacagtg cgtggaagag gccatgcagc cagtggcaga    13680
ttgtggggag gggacggccc agggccacgt tccaggcttg ggaggctgct ccagaccttg    13740
gtagctgaaa gtctcagtgg gaatgagcgt tcagaggcca ggacttgctc ggagaattct    13800
aaccacaccc tgcctgtttt atatgttcag ttttcaaagt aatcaatagc cactataaga    13860
aaaaaacaaa gccactttca aagggttgtg gtaagaggca gtcctgtgag caggccggct    13920
gcagggcctc cagggctgtg gggcaggctg cacagggggct ggtgggtccc atgcctgggg    13980
gtctgggaat agtctctagg ctgctgtcct ggaggaggtt tccccaacg cctgagacca    14040 gggcaccatg tgacccatga ctcacagttg cctggctgag gcaggcactt gttcacctgg    14100
agcctccctg gggcctttcg gggcccgggg gtgtggatag gtggctttgg agccacattt    14160
gtccatcggg acgttgggct cccagctggc cttccgggct ttccctgctc ccagaacctc    14220
cctgctcagc ccttgccagc cttaccctcc ccctccaccc tgcccagcat ggggctctcc    14280
ctgtgtggat gccagaagca gttgggccct cagggctggt cccaggaggt gccccagtg    14340 aggtgctctg cagaaactgc ccagtctggc ctcctgctgt ctgtggcaca gtctgactgt    14400
gtgtggtgag gtccaggcct tctgcctccc acttacctgg cccagggcac agagacctcc    14460
tttccatcct tcctcctggc cccttttcg tgttcccaag gcaggatctc agggtaccag    14520 actaaccccct gttgaacccc aagtttggtg agcttctgga cctccttgag gcccgtgtgc    14580
aaagtcccca gtcaagtgtg cagtcctgac tgctggggcg ttgaccacga agggtgcagg    14640
agcttcacag ccaggcctgg gtgcttcac agtcggggta gagagagcaa tacactagat    14700
gcctcctgtc tgcctggtgg aggccacggg gtcaggatgg tgaatgggcc aagtctggta    14760
gtggggaagt tgtaaacatt tgaaccaccg gacaggcctc atcgggaagc atcagcctaa    14820
ccacaggcca gggacaggcg tctgagcagg cacaggccag ggacaggcgt ccgaccaggc    14880
tcatggctgg ggccaggtgg gccaggtggg ccaggtgggc cggcgatgt gtacacggct    14940 cccttcttgg ctcagctggg cgcgctggga agtgcttggg gtgcctgggc tagactccga    15000
agggcaggga ctcgccgctg gagttgtcca cggagcaggc cctcaaaggt gggagctggg    15060
gccagctctg gaaatagacc cccacagggt cctcatgaga tgtgggggac ccaaggaagt    15120
ccagcaggca gcctcaggtg caggtggggg cagggtggtg tccaggctca gcccacagag    15180
ggtcctgcgg ttggggtgg gctaagggaa ccaggccagg cccaagggga accatgaggg    15240
agggcagtct ggggccactc tgataggaga aggggcaggt ggtctgcggc ctggggacct    15300
gtagcctcac ccctccgtgg ggacctgagg caccagccgg gcactcaccg aagtcatctg    15360
ggacaggctt cacccttccg tgggggcctg aggcaccagc cgggcgccca ccaaagtcat    15420
ctgggagagg cttcacccct ccgtggggc ctgaggcacc agctgggcgc ccaccgaagg    15480
gcttcaacac ttgtgcccag gcccttcgtg caggcccttc gtcagaccca agagtgggcc    15540
tggctctccc cctgcactga tgggactggg gccagagcct gggggccctg atgcctcttg    15600
gtctgagacc ctcagcttag ggtcaggag ggctcaggct gggtgaggcc tgtggtccaa    15660
cgtgccatat ccatctctct acagggcgag gctggcccta tcggacctaa aggctaccga    15720
```

```
ggcgatgagg gtcccccagg gtccgaggtg agtcccactc cccacccaca cccgcccacc   15780 cagggggggcc tgaggatcca gaacccactg tctgcccagt gctggccccg tgccctctga   15840
ggactctatg gccctgggtg tcctggctcc cgatgggacc tctcccggcc ccaggagggc   15900
cctgcttccc tccaaggtca ccatgctaag cctgctcccc tcacgcctcc tcttcctcct   15960
cagggtgcca gaggagcccc aggacctgcc ggaccccctg gagacccggg gctgatgggt   16020
gaaagggtga gtgtccaaca gctcgggccc tagggcggag gcctggccgc cagaggccct   16080
gggaagcccc agccccgcac tgtggagctg cctgggtcc ctgaccgggc cgggagtgcc   16140
cgcagcatca ctggctcctg gccacagtcg gcacctgagc cagaggccgc ctcggcaggg   16200
cccctcctgc cccgagatcc gggtcccagg gtccacgggg accagcaggg tggccccagg   16260
ggagggagcc ggcttctggg ctgacggagg ggccctgcgg gtgaggtgct cccgggcctg   16320
tgccagccag tgggtatccc aggccaggcc gattcgcacg gtgacggcta ctctgctccc   16380
ccagggagaa gacggccccg ctggaaatgg caccgagggc ttccccggct tccccgtaag   16440
tgtccggagg ctgagcccac aggaacatgc ccaagctgcc tgcggcgccc tctttagtgg   16500
actgggcact cttgggtggg cgggctggcc ccaggaccgc cggctggccc aggaattcca   16560
tggccgggat tctgtcagct caggcccttc cgctgtgcgc ccctcacagc ctcccctctc   16620
aaatcagaac ccggtatcac tgccctgctt ttccatgaca ggggtatccg ggcaacaggg   16680
gcgctcccgg gataaacgtg agtacgcccc ctcctccatc tggctgtggg cacacaaaca   16740
ttcacagtca cagggacacg cacgtgtgaa cacacatgtg cacacaggct cccgagcaaa   16800
cacacggggt acacaggcac ccacggctgc cccactgtct gtggccacag ccccagttgg   16860
catcggctcc tgcaggccct gcgaggctcc cactgtggtg tggcctgtgg gtctcctcac   16920
ggccctgact gccggtgac cgatctcccc tcggtgcgca gggcaggccc agccccagag   16980 gccgcccac ggctctctag gccactccgg gacccagttt ctccagccca ggaaatgtgt   17040
gtggtggggg aagggaagag aagagtgcct ctcttatctt tatttttttc cttttaaaat   17100
ttccacttcc taaaaacaaa ataaaaccct tgttaaccaa gtgctctccc gtcactgcag   17160
ggcacgaagg gctaccccgg cctcaagggg gacgagggag aagccgggga ccccggagac   17220
gatgtaagtg tggatgggag gcagggccag ccccaagtcc acctgagcca gagggctggg   17280
cccttgaagg gcagtggacc aggaccccgct tgggaggcc tcatgggccc cggctgctgg   17340
atgctctgtg gacggggcca gcgcgcagat gcccgggtgg tgcacggtct gttgacacaa   17400
cgctgttccc ttctagaaca acgacattgc accccgagga gtcaaaggag caaagggta   17460 ccggggtccc gagggccccc aggtgggtgg atgtggctgg gtgaggccac ggtgggctgt   17520
gcctgggacg ccggatgctg gggctgggga atgctgaaag aggctgggag agtgggaggc   17580
ggcgggaggg aattttgggg agcacgtcat ctggaggcc ctgggggtgg gaggtgccgg   17640
tcaccagggc caggtggtgg ccagggcagc agagccgagc ccaggacac agcgggtcct   17700 cagggtgggg cccacctggg atggccgcct ggaccaccag tgtgcgaagc cccagctgcc   17760
ctcacagcac cgtcactgga ggacgagggg ctgggtaggg agggaccggg caggggtggg   17820
cttgatgagg ggcagggccc tggggtggg ggctgtctca gctcaggaag cacagtgggc   17880 tcctcacccct cagagctcct ctactccgtt tctcggacag ggaccccccag gacaccaagg   17940 accgcctggg ccggacgtaa gtggggctct gtgaacattg ctgggggcga ccactgtagc   18000
ttccatccct tggggtgtgg gtcctgtcca tgggtgctcc tgtagacgct gctcacgggg   18060
gggtgggttg tggacaaaga gctggtgcca ggccctaggg acccgtgacg gccatgggag   18120
```

```
gacccgtgag gatcataggg ggatgtgtga ggaccataga ggggacatgt gaggatcatg   18180
ggggacatgt gaggatcatg gggggggacgt gtgaggatca tgggaggacg tgaggatcat   18240 ggaggggggac atgtgaggat catgggggac ccgtgaggat catgggggac ccgtgtgagg   18300 atcatgggg gggacgtgtg aggatcatgg ggggacctgt acccatgagg accatgaggg   18360
gacccgtgac ggccacgggg agacccatga ctgcgctgtt tctatgacca cgtcaggggt   18420
ccagcccagt agcaggggtg tagtgggcag agccgggcac acctgcaaag aacctcctgc   18480
ccaaaccccg ccctgtgggg gccccaggga gggtgacctg gagatccagc agcccacagt   18540
ccccgctggg aggggctgtc tatggcccca gtaccctcgt ctctccctcc ccaggaatgc   18600
gagattttgg acatcatcat gaaaatgtgc tgtgagtatc tctgagaagc cgtcctcgtt   18660
agggagagca gggccgccag cctggcctgt tccactccta gaagggtgtc tccactgttg   18720
ggggcctggg tctctgggta catccttgag gaggctcctc agccagcccc taccggcctc   18780
caaagccctc ccaggccccc gggtccccgc acaggctgag agtccccggt gcggtgcaga   18840
gctgccacgt ggggagggcg gccggggagg cggggaggcg gggcaggagg ccggggaagg   18900
ggggaggccg gggaaggagg gcggccgggg aggcggggag gctgccccaa gagtaaaagc   18960
ctttctgacg tgcgcaggac gcggccctga ctggtctaac tgactctttc tcttctcctc   19020
agcttgctgt ggtgagaccc aggctctagc tcctgagaga atggatcccg ggggtcgggg   19080
agcgaggcct gggtcccaca catgtcacag gacagcacat ggcactctgg tccccgcccg   19140
cagctccctg cacctgcccg cccctctgg ggcctgctcc aagccagcag ggttcccggg   19200
tgttgggctg ggccccgccc tctttcaccc ataactgaaa taaccaggag caggcttggg   19260
ggggtccctg ctccatcatt ctggcccaca ggccccaccc tagcctggct gagcaacgcc   19320
agccctgacc agccgccgga cagagcagcc tttacggggc catgggaggg ggtgggcttt   19380
tctggggctg agacgggggg accccaacgt gtcaggtgag gatgtggcag ccaaggaggg   19440
gccagggcgg tggaggggag gggccagggc actggagggg aggggcgtgc tctgctgaca   19500
ccgcccccgc ctgcagaatg caagtgcggc cccatcgacc tcctgttcgt gctggacagc   19560
tcagagagca ttggcctgca gaacttcgag attgccaagg acttcgtcgt caaggtcatc   19620
gaccggctga gccgggacga gctggtcaag gtgaggcctc gccccgcccg gctttctcaa   19680
gcccaggtgc acccccgaccc tgccggccgc ccctgcccgc gccagacctc agcctcccga   19740
ggccaccgct gcatccctgt gacttcccta ctcatgacaa ggatgccagg cacgcgccag   19800
cccgtccagg cctccagctc cacctggcga ggctggccca ttgtacacag gcgccccaga   19860
tgagggaggg tctccccctc tccttgaagg gcggtagtct ggggtcctga gtgctgggtg   19920
tgggcttgtc cctcgtggac agaacccagg agggcttcat ccaccaagga agattgcttt   19980
gcagggtacc caggtcccgg gggctgtgcc accctctggg caccccggagc caatcgcagg   20040 gtacccaggt cccgggggct gtgccaccct ctgtgcaccc agagccaatc gcaggggacc   20100
caggtcctga ggtcctgggg gccatgccac cctctgggca cccgcagcca atagagtcac   20160
ccttgggaag cttatgcgga cctggggcag cactcgcgtc ctgacccggg tgccggtccc   20220
acagttcgag ccagggcagt cgtacgcggg tgtggtgcag tacagccaca gccagatgca   20280
ggagcacgtg agcctgcgca gccccagcat ccggaacgtg caggagctca aggagtgagt   20340
gccccacgcg gccaggaccc tcccacccct cgccccgacc gctgttccca cggcaggtcg   20400
gccctgaccc ctgatcccag gtgggctcgg ccccgcggca ggcctggccc caaccggccc   20460
```

```
ttcctgccct tgctatgca gagccatcaa gagcctgcag tggatggcgg gcggcacctt    20520
cacgggggag gccctgcagt acacgcggga ccagctgctg ccgcccagcc cgaacaaccg    20580
catcgccctg gtcatcactg acgggcgctc agacactcag agggacacca caccgctcaa    20640
cgtgctctgc agccccggca tccaggtggg gtggccaccc ccaggctgca cctgccccgc    20700
ctagggcgcc ccgccagcca gggtggcctt gtccccagaa agacgagggc agagcaggct    20760
gcgccacacc gatactgtct gtccccacag gtggtctccg tgggcatcaa agacgtgttt    20820
gacttcatcc caggctcaga ccagctcaat gtcatttctt gccaaggcct ggcaccatcc    20880
cagggccggc ccgcctctc gctggtcaag gagaactatg cagagctgct ggaggatgcc    20940
ttcctgaaga atgtcaccgc ccagatctgc ataggtgcgc atggggccac ccgggcagtc    21000
ccagatctgc gtaggtgcgc gcggggccgc ccgggcagtc ccagatctgc gtaggtgcac    21060
gcggggccgc ccgggcagtc ccagatctgc gtaggtgcac gcggggccgc ccagggccgt    21120
cccagatctg tgtaggtgcg cgcaggcgcc caggctgtc ccagaggcct cctcccagct    21180
cactgttacc tccaggggca cggccaccct gtaggtgcgc acggggccgc ctggggctgt    21240
cccacaggca tcctcctccc ggctcgctgt gacttccggg ggcacggcca cccctgtgct    21300
cggccgggag gtcctgtgac atctccttgc ggggttatag gtggagcagt gggctcacac    21360
tgcacggctt ttctctttta cagacaagaa gtgtccagat tacacctgcc ccagtgagta    21420
cctcggcggc cgggacacgt ggggaggagg gcaccgtggt tggggcgagg gctctgagag    21480
gacggggctc tgggaggagg gcctggcggt cacgagagta ggtgcatggc tcactccggt    21540
ggctgagcac caccgtgccg tgccctctct ggggagctta gacgctctct ggccggccca    21600
ctgcggctgc atcaccaggg cctcatgcta acggctgccc accccgcccc gcagtcacgt    21660
tctcctcccc ggctgacatc accatcctgc tggacggctc cgccagcgtg ggcagccaca    21720
actttgacac caccaagcgc ttcgccaagc gcctggccga gcgcttcctc acagcgggca    21780
ggacggaccc cgcccacgac gtgcgggtgg cgtggtgca gtacagcggc acgggccagc    21840
agcgcccaga gcgggcgtcg ctgcagttcc tgcagaacta cacggccctg ccagtgccg    21900
tcgatgccat ggactttatc aacgacgcca ccgacgtcaa cgatgccctg ggctatgtga    21960
cccgcttcta ccgcgaggcc tcgtccggcg ctgccaagaa gaggctgctg ctcttctcag    22020
atggcaactc gcagggcgcc acgcccgctg ccatcgagaa ggccgtgcag gaagcccagc    22080
gggcaggcat cgagatcttc gtggtggtcg tgggccgcca ggtgaatgag ccccacatcc    22140
gcgtcctggt caccggcaag acggccgagt acgacgtggc ctacgcgag agccacctgt    22200
tccgtgtccc cagctaccag gccctgctcc gcggtgtctt ccaccagaca gtctccagga    22260
aggtggcgct gggctagccc accctgcacg ccggcaccaa accctgtcct cccacccctc    22320
cccactcatc actaaacaga gtaaaatgtg atgcgaattt tcccgaccaa cctgattcgc    22380
tagattttt ttaaggaaaa gcttggaaag ccaggacaca acgctgctgc ctgctttgtg    22440
cagggtcctc cgggctcag ccctgagttg gcatcacctg cgcagggccc tctgggggctc    22500
agccctgagc tagtgtcacc tgcacagggc cctctgaggc tcagccctga gctggcgtca    22560
cctgtgcagg gccctctggg gctcagccct gagctggcct cacctgggtt ccccacccccg    22620
ggctctcctg ccctgccctc ctgccgccc tccctcctgc ctgcgcagct ccttccctag    22680
gcacctctgt gctgcatccc accagcctga gcaagacgcc ctctcgggggc ctgtgccgca    22740
ctagcctccc tctcctctgt ccccatagct ggttttccc accaatcctc acctaacagt    22800
tactttacaa ttaaactcaa agcaagctct ctcctcagc ttggggcagc cattggcctc    22860
```

```
tgtctcgttt tgggaaacca aggtcaggag gccgttgcag acataaatct cggcgactcg   22920
gccccgtctc ctgagggtcc tgctggtgac cggcctggac cttggcccta cagccctgga   22980
ggccgctgct gaccagcact gaccccgacc tcagagagta ctcgcagggg cgctggctgc   23040
actcaagacc ctcgagatta acggtgctaa ccccgtctgc tcctccctcc cgcagagact   23100
ggggcctgga ctggacatga gagcccttg tgccacaga gggctgtgtc ttactagaaa      23160
caacgcaaac ctctccttcc tcagaatagt gatgtgttcg acgttttatc aaaggccccc    23220
tttctatgtt catgttagtt ttgctccttc tgtgtttttt tctgaaccat atccatgttg   23280
ctgacttttc caaataaagg ttttcactcc tctc                                23314
```

<210> SEQ ID NO 2
<211> LENGTH: 1028
<212> TYPE: PRT
<213> ORGANISM: Homo sapiens
<400> SEQUENCE: 2

```
Met Arg Ala Ala Arg Ala Leu Leu Pro Leu Leu Gln Ala Cys Trp
1               5                   10                  15

Thr Ala Ala Gln Asp Glu Pro Glu Thr Pro Arg Ala Val Ala Phe Gln
                20                  25                  30

Asp Cys Pro Val Asp Leu Phe Phe Val Leu Asp Thr Ser Glu Ser Val
            35                  40                  45

Ala Leu Arg Leu Lys Pro Tyr Gly Ala Leu Val Asp Lys Val Lys Ser
        50                  55                  60

Phe Thr Lys Arg Phe Ile Asp Asn Leu Arg Asp Arg Tyr Tyr Arg Cys
65                  70                  75                  80

Asp Arg Asn Leu Val Trp Asn Ala Gly Ala Leu His Tyr Ser Asp Glu
                85                  90                  95

Val Glu Ile Ile Gln Gly Leu Thr Arg Met Pro Gly Gly Arg Asp Ala
            100                 105                 110

Leu Lys Ser Ser Val Asp Ala Val Lys Tyr Phe Gly Lys Gly Thr Tyr
        115                 120                 125

Thr Asp Cys Ala Ile Lys Lys Gly Leu Glu Gln Leu Leu Val Gly Gly
    130                 135                 140

Ser His Leu Lys Glu Asn Lys Tyr Leu Ile Val Val Thr Asp Gly His
145                 150                 155                 160

Pro Leu Glu Gly Tyr Lys Glu Pro Cys Gly Gly Leu Glu Asp Ala Val
                165                 170                 175

Asn Glu Ala Lys His Leu Gly Val Lys Val Phe Ser Val Ala Ile Thr
            180                 185                 190

Pro Asp His Leu Glu Pro Arg Leu Ser Ile Ile Ala Thr Asp His Thr
        195                 200                 205

Tyr Arg Arg Asn Phe Thr Ala Ala Asp Trp Gly Gln Ser Arg Asp Ala
    210                 215                 220

Glu Glu Ala Ile Ser Gln Thr Ile Asp Thr Ile Val Asp Met Ile Lys
225                 230                 235                 240

Asn Asn Val Glu Gln Val Cys Cys Ser Phe Glu Cys Gln Pro Ala Arg
                245                 250                 255

Gly Pro Pro Gly Leu Arg Gly Asp Pro Gly Phe Glu Gly Glu Arg Gly
            260                 265                 270

Lys Pro Gly Leu Pro Gly Glu Lys Gly Glu Ala Gly Asp Pro Gly Arg
        275                 280                 285
```

-continued

| | | | | | | | | | | | |
|---|---|---|---|---|---|---|---|---|---|---|---|
|Pro|Gly|Asp|Leu|Gly|Pro|Val|Gly|Tyr|Gln|Gly|Met|Lys|Gly|Glu|Lys|
|290| | | | |295| | | | |300| | | | | |

Gly Ser Arg Gly Glu Lys Gly Ser Arg Gly Pro Lys Gly Tyr Lys Gly
305                 310                 315                 320

Glu Lys Gly Lys Arg Gly Ile Asp Gly Val Asp Gly Val Lys Gly Glu
                325                 330                 335

Met Gly Tyr Pro Gly Leu Pro Gly Cys Lys Gly Ser Pro Gly Phe Asp
            340                 345                 350

Gly Ile Gln Gly Pro Pro Gly Lys Gly Asp Pro Gly Ala Phe Gly
        355                 360                 365

Leu Lys Gly Glu Lys Gly Glu Pro Gly Ala Asp Gly Glu Ala Gly Arg
370                 375                 380

Pro Gly Ser Ser Gly Pro Ser Gly Asp Glu Gly Gln Pro Gly Glu Pro
385                 390                 395                 400

Gly Pro Pro Gly Glu Lys Gly Glu Ala Gly Asp Gly Asn Pro Gly
                405                 410                 415

Pro Asp Gly Ala Pro Gly Glu Arg Gly Gly Pro Gly Arg Gly Pro
            420                 425                 430

Arg Gly Thr Pro Gly Thr Arg Gly Pro Arg Gly Asp Pro Gly Glu Ala
        435                 440                 445

Gly Pro Gln Gly Asp Gln Gly Arg Glu Gly Pro Val Gly Val Pro Gly
450                 455                 460

Asp Pro Gly Glu Ala Gly Pro Ile Gly Pro Lys Gly Tyr Arg Gly Asp
465                 470                 475                 480

Glu Gly Pro Pro Gly Ser Glu Gly Ala Arg Gly Ala Pro Gly Pro Ala
                485                 490                 495

Gly Pro Pro Gly Asp Pro Gly Leu Met Gly Glu Arg Gly Glu Asp Gly
            500                 505                 510

Pro Ala Gly Asn Gly Thr Glu Gly Phe Pro Gly Phe Pro Gly Tyr Pro
        515                 520                 525

Gly Asn Arg Gly Ala Pro Gly Ile Asn Gly Thr Lys Gly Tyr Pro Gly
530                 535                 540

Leu Lys Gly Asp Glu Gly Glu Ala Gly Asp Pro Gly Asp Asp Asn Asn
545                 550                 555                 560

Asp Ile Ala Pro Arg Gly Val Lys Gly Ala Lys Gly Tyr Arg Gly Pro
                565                 570                 575

Glu Gly Pro Gln Gly Pro Pro Gly His Gln Gly Pro Pro Gly Pro Asp
            580                 585                 590

Glu Cys Glu Ile Leu Asp Ile Ile Met Lys Met Cys Ser Cys Cys Glu
        595                 600                 605

Cys Lys Cys Gly Pro Ile Asp Leu Leu Phe Val Leu Asp Ser Ser Glu
610                 615                 620

Ser Ile Gly Leu Gln Asn Phe Glu Ile Ala Lys Asp Phe Val Val Lys
625                 630                 635                 640

Val Ile Asp Arg Leu Ser Arg Asp Glu Leu Val Lys Phe Glu Pro Gly
                645                 650                 655

Gln Ser Tyr Ala Gly Val Val Gln Tyr Ser His Ser Gln Met Gln Glu
            660                 665                 670

His Val Ser Leu Arg Ser Pro Ser Ile Arg Asn Val Gln Glu Leu Lys
        675                 680                 685

Glu Ala Ile Lys Ser Leu Gln Trp Met Ala Gly Gly Thr Phe Thr Gly
690                 695                 700

Glu Ala Leu Gln Tyr Thr Arg Asp Gln Leu Leu Pro Pro Ser Pro Asn

```
                705                 710                 715                 720
        Asn Arg Ile Ala Leu Val Ile Thr Asp Gly Arg Ser Asp Thr Gln Arg
                        725                 730                 735

Asp Thr Thr Pro Leu Asn Val Leu Cys Ser Pro Gly Ile Gln Val Val
                        740                 745                 750

Ser Val Gly Ile Lys Asp Val Phe Asp Phe Ile Pro Gly Ser Asp Gln
                        755                 760                 765

Leu Asn Val Ile Ser Cys Gln Gly Leu Ala Pro Ser Gln Gly Arg Pro
                        770                 775                 780

Gly Leu Ser Leu Val Lys Glu Asn Tyr Ala Glu Leu Leu Glu Asp Ala
        785                 790                 795                 800

Phe Leu Lys Asn Val Thr Ala Gln Ile Cys Ile Asp Lys Lys Cys Pro
                        805                 810                 815

Asp Tyr Thr Cys Pro Ile Thr Phe Ser Ser Pro Ala Asp Ile Thr Ile
                        820                 825                 830

Leu Leu Asp Gly Ser Ala Ser Val Gly Ser His Asn Phe Asp Thr Thr
                        835                 840                 845

Lys Arg Phe Ala Lys Arg Leu Ala Glu Arg Phe Leu Thr Ala Gly Arg
                        850                 855                 860

Thr Asp Pro Ala His Asp Val Arg Val Ala Val Val Gln Tyr Ser Gly
        865                 870                 875                 880

Thr Gly Gln Gln Arg Pro Glu Arg Ala Ser Leu Gln Phe Leu Gln Asn
                        885                 890                 895

Tyr Thr Ala Leu Ala Ser Ala Val Asp Ala Met Asp Phe Ile Asn Asp
                        900                 905                 910

Ala Thr Asp Val Asn Asp Ala Leu Gly Tyr Val Thr Arg Phe Tyr Arg
                        915                 920                 925

Glu Ala Ser Ser Gly Ala Ala Lys Lys Arg Leu Leu Phe Ser Asp
                        930                 935                 940

Gly Asn Ser Gln Gly Ala Thr Pro Ala Ala Ile Glu Lys Ala Val Gln
        945                 950                 955                 960

Glu Ala Gln Arg Ala Gly Ile Glu Ile Phe Val Val Val Gly Arg
                        965                 970                 975

Gln Val Asn Glu Pro His Ile Arg Val Leu Val Thr Gly Lys Thr Ala
                        980                 985                 990

Glu Tyr Asp Val Ala Tyr Gly Glu Ser His Leu Phe Arg Val Pro Ser
                        995                 1000                1005

Tyr Gln Ala Leu Leu Arg Gly Val Phe His Gln Thr Val Ser Arg
                1010                1015                1020

Lys Val Ala Leu Gly
        1025

<210> SEQ ID NO 3
<211> LENGTH: 21
<212> TYPE: DNA
<213> ORGANISM: Artificial
<220> FEATURE:
<223> OTHER INFORMATION: siRNA-F for COL6A1

<400> SEQUENCE: 3
acagugacga gguggagaut t                                              21

<210> SEQ ID NO 4
<211> LENGTH: 21
<212> TYPE: DNA
<213> ORGANISM: Artificial
```

```
<220> FEATURE:
<223> OTHER INFORMATION: siRNA-R for COL6A1

<400> SEQUENCE: 4
aucuccaccu cgucacugut t                                          21

<210> SEQ ID NO 5
<211> LENGTH: 21
<212> TYPE: DNA
<213> ORGANISM: Artificial
<220> FEATURE:
<223> OTHER INFORMATION: siRNA-F for COL6A1

<400> SEQUENCE: 5
gcauuggccu gcagaacuut t                                          21

<210> SEQ ID NO 6
<211> LENGTH: 21
<212> TYPE: DNA
<213> ORGANISM: Artificial
<220> FEATURE:
<223> OTHER INFORMATION: siRNA-R for COL6A1

<400> SEQUENCE: 6
aaguucugca ggccaaugct t                                          21

<210> SEQ ID NO 7
<211> LENGTH: 21
<212> TYPE: DNA
<213> ORGANISM: Artificial
<220> FEATURE:
<223> OTHER INFORMATION: siRNA-F for COL6A1

<400> SEQUENCE: 7
acucaaagca agcucuucut t                                          21

<210> SEQ ID NO 8
<211> LENGTH: 21
<212> TYPE: DNA
<213> ORGANISM: Artificial
<220> FEATURE:
<223> OTHER INFORMATION: siRNA-R for COL6A1

<400> SEQUENCE: 8
agaagagcuu gcuuugagut t                                          21
```